US00PP19512P3

(12) United States Plant Patent
Hauenstein

(10) Patent No.: US PP19,512 P3
(45) Date of Patent: Dec. 2, 2008

(54) VARIETY OF RASPBERRY PLANT NAMED 'RAFZAQU'

(50) Latin Name: *Rubus idaeus*
Varietal Denomination: RAFZAQU

(75) Inventor: Peter Hauenstein, Wasterkingen (CH)

(73) Assignee: Promo-Fruit Ltd., Rafz (CH)

( * ) Notice: Subject to any disclaimer, the term of this patent is extended or adjusted under 35 U.S.C. 154(b) by 146 days.

(21) Appl. No.: 11/241,290

(22) Filed: Sep. 30, 2005

(65) Prior Publication Data

US 2007/0079405 P1 Apr. 5, 2007

(51) Int. Cl.
*A01H 5/00* (2006.01)

(52) U.S. Cl. ..... Plt./204
(58) Field of Classification Search ..... Plt./204
See application file for complete search history.

(56) References Cited

PUBLICATIONS

UPOVROM Citation for 'RAFZAQU'as Per QZ PBR 20001707; Nov. 28, 2000.*

UPOVROM Citation for 'RAFZAQU'as Per CH PBR 00–28–1644; Aug. 24, 2000*

Dialog Printout Only H. Butchter–Weisbrodt; Autumn raspberry cultivar Himbo–Top. Presentation and first experiences; Obstbau 26(1); pp. 35–36; 2001..*

* cited by examiner

*Primary Examiner*—Kent L Bell
(74) *Attorney, Agent, or Firm*—Christie, Parker & Hale, LLP.

(57) ABSTRACT

A new and distinct variety of raspberry plant, designated 'RAFZAQU', characterized by large, firm, easily detachable fruit with excellent flavor, medium spine density on very young shoots, free to touching lateral leaflets and a medium time of ripening on canes.

2 Drawing Sheets

Classification: The variety is botanically known as *Rubus idaeus*.

Varietal denomination: The new raspberry plant has the varietal name of 'RAFZAQU'.

SUMMARY OF THE INVENTION

The present invention relates to a new and distinct variety of raspberry plant designated as 'RAFZAQU'. This new variety is a result of a controlled cross between the fall raspberry variety 'AUTUMN BLISS' (U.S. Plant Pat. No. 6,597) and the summer raspberry variety 'RAFZETER' (not patented in the United States; sold as HIMBO QUEEN).

The new variety is a fall variety, having strong growth, producing fewer runners (stolons) than 'AUTUMN BLISS', and having similar resistance to *Phytophtora* as 'AUTUMN BLISS'. The fruit of the new variety is very large compared to most unknown commercial varieties, on the order of six to 8 grams, and is firm, easy to transport, brilliant red in color, without darkening after harvest, conical in shape, and easily detachable with excellent flavor. Fruit of the new variety can be harvested in mid-Switzerland from about August 20 (i.e., approximately 2 weeks after 'AUTUMN BLISS'), for a duration of 6 to 7 weeks.

After its selection, the new variety was asexually propagated by cuttings and extensively tested in fruiting fields. This propagation has demonstrated that the combination of traits disclosed herein as characterizing the new variety are fixed and remain true to type through successive generations of asexual reproduction.

COMPARISON TO CLOSEST COMMERCIAL CULTIVAR

TABLE 1

The new variety differs from the commercial cultivar 'AUTUMN BLISS' as follows:

| | 'AUTUMN BLISS' | 'RAFZAQU' |
|---|---|---|
| Young shoot - density of spines in central third | Dense to very close | Medium |
| Leaf - overlapping of leaflets | Touching to overlapping | Free to touching |
| Time of ripening on canes | Very early to early | Medium |
| Fruit Color | The fruit is rather dark colored. They become even darker after they have been cropped. | The fruit is light red both on the plant and after cropping. |
| Number of young canes | Produceds numerous young canes | Produces relatively few young canes |
| Length of one year old canes | The one-year old canes are approximately 2 meters long | The one-year old canes approximately 2.50 to 3 meters long |
| Fruit cropping | The beginning of the fruit cropping is early August | Fruit cropping starts around August 10/20 |

COMPARISON WITH THE 'RAFZETER' CULTIVAR

'RAFZETER' is a "summer" raspberry (it bears fruit on the 2-year old wood). Crop is in July. 'RAGZAQU' is a "Fall" (Autumn) primocane raspberry and bears fruit both on 1-year old and 2-year old wood; small crop on first year canes in mid-June and second crop from August 10 (local conditions at breeder's place).

'RAFZETER' is very prone to phytophtora fragriae while 'RAFZAQU' is highly resistant to that type of fungi.

'RAFZETER' produces 2.50 m canes while 'RAFZAQU' produces up to 3 m long.

BRIEF DESCRIPTION OF THE DRAWINGS

The accompanying color photographs show a typical specimen of the new variety as nearly true as it is possible to make in color reproductions.

DETAILED DESCRIPTION OF THE INVENTION

Figure 1:
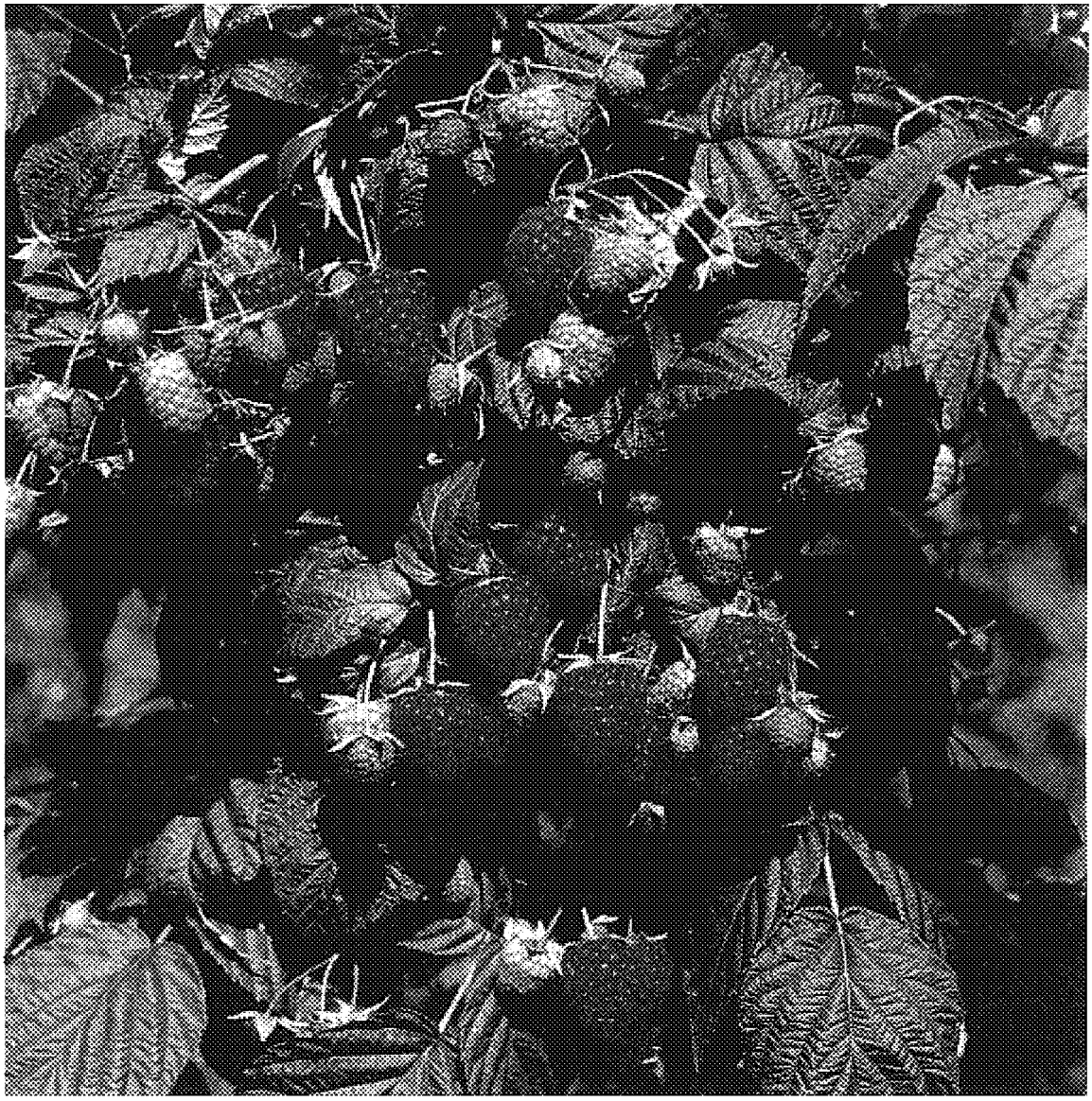
FIG. 1 is a photograph of the leaves and fruit of the new variety.
Figure 2:
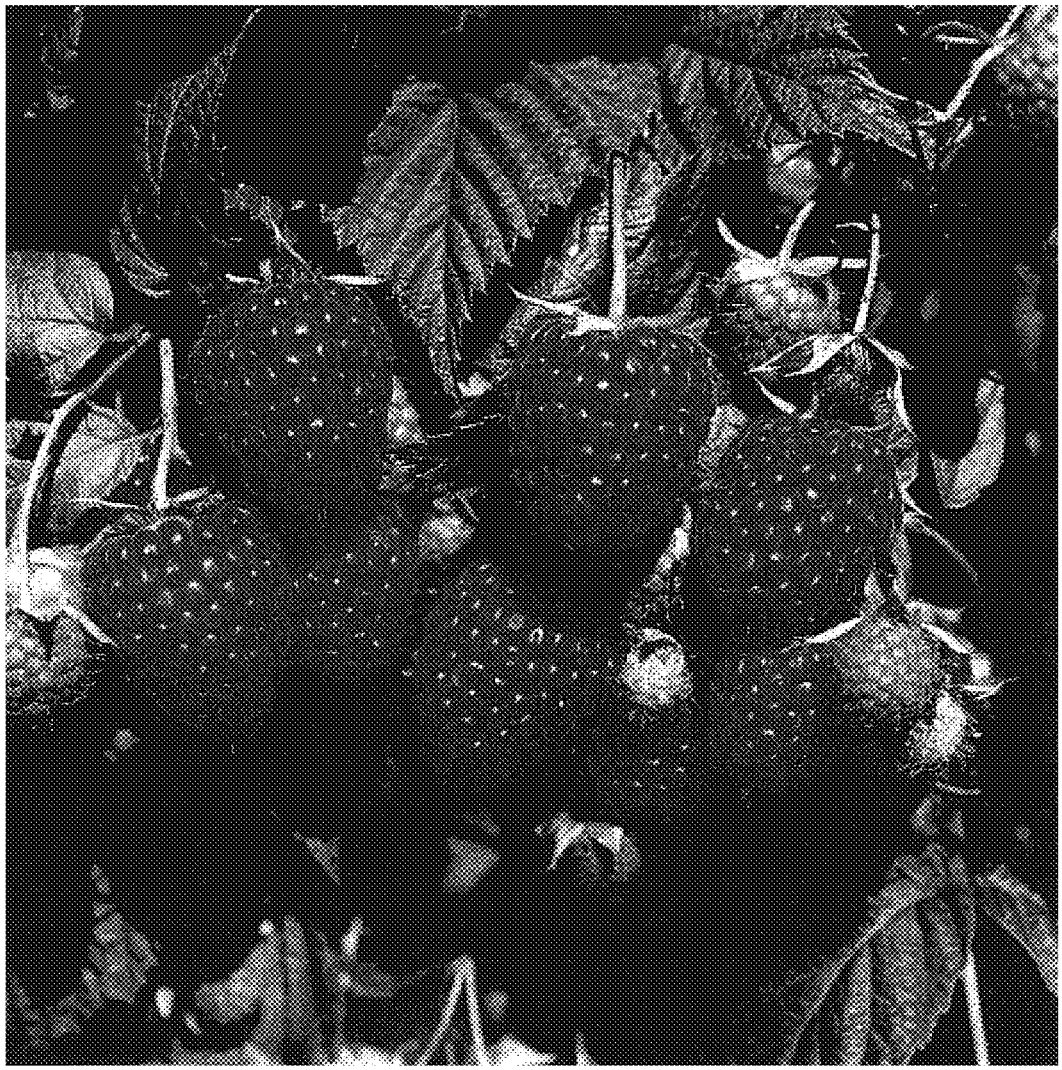
FIG. 2 is a close-up photograph of fruit of the new variety.

The phenotypical descriptions, measurements and color designations stated for the new variety 'RAFZAQU' may vary, depending upon variations in environmental factors, including weather (temperature, humidity and light intensity), day length, soil type, location and cultural conditions. 'RAFZAQU' has not been observed under all possible environmental conditions, however, the observations listed were made at the location of the breeder in Rafz, Kanton Z ÜRICH, northeast of Switzerland at an altitude of approximately 430 meters above sea level in a field which is located in a slope of land with a heavy, loamy soil.

Shoots:

*Anthocyanin coloration of very young shoots.*—Present.

*Intensity of anthocyanin coloration of very young shoots.*—Weak to medium.

*Number of young shoots.*—Few.

*Spines on young shoots.*—Present.

*Bloom on full grown shoot.*—Weak.

*Time of shoot emergence.*—Medium. The lateral shoots are very long and can reach up to 80 cm. The fruit bearing side shoots start at approximately 40 cm above the ground. In order to avoid breakage, the side shoots should be tied and propped up. The color of the side shoots is RHS (fan 3) No 145C.

Spines:

*Density of spines in central third of young shoot.*—Sparse.

*Color of spines on young shoots.*—Purple. The lower spines are fairly numerous. At the top of the young canes there are practically no spines (5–7 for each 5 cm). The spines are very short and do not interfere negatively with plucking of the berries and are not noticeable at the fruit stands.

*Cane.*—Length. Long.

*Time of ripening on canes.*—Very early to early.

Leaves:

*Leaf.*—Relief between the veins Medium.

*Leaf.*—Number of leaflets Sometimes three, sometimes five.

*Leaf.*—Overlapping of lateral leaflets Touching.

*Leaf.*—Color of upperside Dark green.

*Lateral leaflet.*—Length of stalklet (lower pair) Very short. The general color of the leaves is RHS 3rd Fan blue-green; Green; Yellow-green groups based upon the R.H.S. Colour Chart (of The Royal Horticultural Society in London, England).

*Upperside leaves.*—144 A.

*Underside.*—138 B. The shape of the leaves is oval and terminates in a pointed shape. The leaves are very sharply indented. The leaf veins are on the upper side and are of a lighter color than the leaf itself. The leaf veins are very marked on the underside. The main leaf is approximately 13 cm long. The stipules are approximately 6 cm broad and 10 cm long. The leaves on the lower part of the young canes have an average of 4 stipules. The average total length of the petiole (Blattrieb) is 35/40 cm. The distance from the leaf axil to the first side leaves is approximately 14 cm. From there on to the second side leaves, the distance is approximately 7 cm. The distance from the second side leaves to the central leaf is approximately 4 cm.

Flower:

*Flower.*—Size Large.

*Flower.*—Anthocyanin coloration of pedicel Present.

*Flower.*—Intensity of anthocyanin coloration of pedicel Weak. The diameter of the flower is approximately 20 mm petals per flower.

Petals: Each petal is approximately 8/9 mm. The form of the petals is generally oveal with a rounded edge. The upper/under side of the petals is white. The blooms have no anthocyanin coloration.

Sepals: The sepals are very pointed and approximately 15 mm long. At the time of blooming they are strongly bent forward. At the end of blooming they bend backwards. The color of the sepals is RHS (fan 3) No 142 C on the upperside and No 142 A on the underside.

*Number of sepals.*—5.

Fruit:

*Fruiting lateral length.*—Medium.

*Fruit.*—Color Pale red (Red Group No. 47A).

*Fruit.*—Size Large.

*Fruit.*—Length:width ratio Longer than broad.

*Fruit.*—Firmness Firm.

*Fruit.*—Glossiness Strong.

*Fruit.*—Adherence to plug Medium.

*Season of fruiting.*—Autumn.

*Length of harvest.*—Medium to long.

What is claimed is:

1. A new and distinct variety of *Rubus idaeus* plant, identified as 'RAFZAQU', substantially as shown and described.

* * * * *

UNITED STATES PATENT AND TRADEMARK OFFICE

CERTIFICATE OF CORRECTION

PATENT NO. : PP 19,512 P3
APPLICATION NO. : 11/241290
DATED : December 2, 2008
INVENTOR(S) : Peter Hauenstein It is certified that error appears in the above-identified patent and that said Letters Patent is hereby corrected as shown below:

On the Title Page

(54) TITLE, line 1 Delete "PLANT"

Signed and Sealed this

Ninth Day of June, 2009

JOHN DOLL
*Acting Director of the United States Patent and Trademark Office*